(12) United States Patent
Dalvi (10) Patent No.: US 11,058,533 B2
(45) Date of Patent: Jul. 13, 2021

(54) EXOCAPSULAR DEVICE AND METHOD FOR LENS STABILIZATION

(71) Applicant: Rajesh Dalvi, Mumbai (IN)

(72) Inventor: Rajesh Dalvi, Mumbai (IN)

(73) Assignee: Rajesh Dalvi, Mumbai (IN)

( * ) Notice: Subject to any disclaimer, the term of this patent is extended or adjusted under 35 U.S.C. 154(b) by 0 days.

(21) Appl. No.: 16/111,010

(22) Filed: Aug. 23, 2018

(65) Prior Publication Data

US 2019/0133754 A1 May 9, 2019

Related U.S. Application Data

(62) Division of application No. 14/748,441, filed on Jun. 24, 2015, now abandoned.

(60) Provisional application No. 62/077,243, filed on Nov. 9, 2014.

(51) Int. Cl.
*A61F 2/16* (2006.01)

(52) U.S. Cl.
CPC .............. *A61F 2/16* (2013.01); *A61F 2/1694* (2013.01); *A61F 2002/1681* (2013.01); *A61F 2002/16902* (2015.04)

(58) Field of Classification Search
CPC .... A61F 2/147; A61F 2/16; A61F 2002/1681; A61F 2/1694
See application file for complete search history.

(56) References Cited

U.S. PATENT DOCUMENTS

| 5,843,184 A | * | 12/1998 | Cionni | ................... | A61F 2/1694 623/4.1 |
| 6,413,277 B1 | * | 7/2002 | Neuhann | ................ | A61F 2/1694 623/6.11 |
| 2006/0235515 A1 | * | 10/2006 | Chassain | ................ | A61F 2/1694 623/6.16 |
| 2012/0290086 A1 | * | 11/2012 | Malyugin | ................ | A61F 9/007 623/6.39 |

FOREIGN PATENT DOCUMENTS

DE                19637692 A1 *  3/1998  ........... A61F 2/1694

\* cited by examiner

*Primary Examiner* — Leslie Lopez (57) ABSTRACT

A device for implantation into an eye for supporting an intraocular lens during and following surgery. The device may include a ring and at least one support. The ring may have an open portion defined between a first eyelet on a first end and a second eyelet on a second end, the ring being radially compressible. The at least one support may be defined internally of the ring and have a position on which a lens is nestably engaged with the at least one support above a tear in the capsular bag of the eye.

8 Claims, 6 Drawing Sheets

EXOCAPSULAR DEVICE AND METHOD FOR LENS STABILIZATION

CROSS REFERENCE TO RELATED APPLICATIONS

The present application is a divisional application of U.S. patent application Ser. No. 14/748,441, now abandoned, which claims priority from U.S. Provisional patent application No. 60/077,243.

TECHNICAL FIELD

The present disclosure relates generally to a device for implantation into an eye. More specifically, the present disclosure relates to a device including a ring and a support for implantation into the ciliary sulcus for stabilizing an artificial IOL lens during and after intraocular surgery.

BACKGROUND

Various diseases and abnormalities exist that can lead to impaired vision in the human eye. Cataract formation is a leading cause of reversible blindness in the world. Cataracts are caused by a gradual clouding of the lens over an extended period and may result in complete loss of functional vision.

The human eye includes a compressible lens enveloped by a capsular bag, which is attached to the ciliary muscles by zonules in a 360 degree circle. Intracapsular cataract extraction involving complete removal of the lens, the capsular bag enveloping the lens, and the zonules connecting the capsular bag to the scleral wall of the eye was the standard surgical procedure approximately four decades ago.

Advances in surgery lead to the development of extracapsular cataract extraction, which is performed to remove the cataractous lens while leaving the capsular bag and zonules substantially intact within the posterior chamber of the eye. In this procedure, a capsulorhexis incision is typically performed to remove a generally circular mid-portion of the anterior capsule of the capsular bag, usually leaving the posterior capsule, an annular anterior capsular flap and a generally circular anterior capsulorhexis edge. The cataractous lens is removed from the residual capsular bag and replaced with an artificial intraocular lens (IOL). The IOL customarily includes haptics for engaging an inner peripheral surface of the residual capsular bag and centralize the IOL within the capsular bag.

Those skilled in the art of ophthalmic surgical procedures will appreciate that the capsular bag is a delicate elastic membrane that envelops the lens. The capsular bag is connected to the scleral wall of the eye through zonule fibers that function to centralize the lens behind the iris and in alignment with the pupil.

In eye patients with missing or damaged zonules from trauma or disease, the position of the capsular bag within the posterior chamber of the eye is unstable, making removal of the enclosed cataractous lens difficult and implantation of the IOL challenging.

Rupture of the capsular bag is a relatively common phenomenon even in modern day cataract surgery, and involves a tear in the anterior capsule or posterior capsule or both. In absence of capsular support it is difficult to place an IOL lens in the eye safely. In cases where there is only a posterior capsular rupture, IOL lenses are routinely placed in the sulcus over the annular anterior capsule. However in scenarios where the annular anterior capsule is also ruptured, this becomes untenable.

When the annular anterior capsule is also ruptured, an IOL is then implanted in the anterior chamber of the eye, with the haptics of the IOL being received in the anterior chamber angle region between the iris and the cornea. Alternatively, the IOL can be sutured to the iris or scleral wall in the posterior chamber, with the haptics of the IOL resting between the iris and the ciliary body. In patients that have had a capsulorhexis tear occurring during phacoemulsification, not only is implantation of the lens more difficult, but the tear and/or missing portion of the capsular bag may allow the IOL to shift or drift into the vitreous of the eye or be decentralized, which would obviously affect vision. The device described herein is particularly adapted to be implanted in the sulcus of an eye for long-term stabilization of the IOL both during and after intraocular surgery.

Notwithstanding the advancements made in the prior art in the field of alternative IOL lenses, there remains a need for an implant which improves stabilization of the intraocular environment during and after intraocular surgery Further, a need exists for a device which enables precise and stable implantation of the IOL lens in the sulcus in spite of a torn capsule, while minimizing the chance of repositioning over time. The ciliary sulcus is a more desirable position for lens implant as compared to the anterior chamber or sclera sutured IOL lenses due to the minimal rate of long term complications.

Hence there is need to provide an implant that provides long-term intraocular lens centration and stabilization in patients having more significant capsular tears. Disclosed herein are one or more devices and methods that advantageously address these issues.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

According to at least one embodiment, a device for implantation into an eye is provided. The device includes a ring and at least one support defined internally of the ring.

According to one or more embodiments, the ring includes an open portion defined between a first eyelet on a first end and a second eyelet on a second end. Further, the ring is radially compressible.

According to one or more embodiments, the ring includes an open portion defined between a first eyelet on a first end and a second end. Further, the ring is radially compressible.

According to one or more embodiments, the at least one support has a position on which a lens is nestably engaged with the at least one support above a tear in the capsular bag of the eye.

According to one or more embodiments, the at least one support defines a first edge engaged with the second end of the ring and extending centrally within the ring to a second edge including a second eyelet.

According to one or more embodiments, the device is made of biocompatible material. In some embodiments, the biocompatible material is polymetheylmethacrylate.

According to one or more embodiments, the at least one support is a first spoke defining a first edge engaged with the ring and extending centrally within the ring to a second edge.

According to one or more embodiments, the first spoke is positioned substantially parallel to the plane formed by the circumference of the ring.

According to one or more embodiments, the first spoke is positioned at an angle relative to the plane formed by the circumference of the ring.

According to one or more embodiments, the device further includes a second spoke positioned approximately 180 degrees from the first spoke along the circumference of the ring and extending centrally.

According to one or more embodiments, the device further includes a plurality of spokes positioned along the circumference of the ring and extending centrally.

According to one or more embodiments, the second edge of the first spoke is engaged with a central point of a segment positioned perpendicular to the first spoke.

According to one or more embodiments, the at least one support is a chord engaged with, and extending between, a third end and a fourth end of the ring.

According to one or more embodiments, the chord is substantially straight and wherein the engagement of the chord and the ring at the third end and fourth end is curved, thereby minimizing risk of further damage to the eye.

According to one or more embodiments, the chord is arced, curved or undulating.

According to one or more embodiments, the chord is positioned substantially parallel to the plane formed by the circumference of the ring.

According to one or more embodiments, at least a portion of the chord is positioned outside of the plane formed by the circumference of the ring.

According to at least one embodiment, a method of implanting a device into an eye is provided. The method includes providing an embodiment of the device, as described herein. The method further includes implanting the device into the ciliary sulcus between the iris and the capsular bag of the eye, the device positioned anterior to a tear in the capsular bag of the eye. The method additionally includes positioning the at least one support proximal to the tear, thereby providing stabilization and centralization to a lens implanted into the eye thereafter.

According to one or more embodiments, the ring of the device is engaged with an interior peripheral surface of the ciliary sulcus.

According to one or more embodiments, the method further includes placing a lens in the ciliary sulcus anterior to, and engaged with, the at least one support.

According to one or more embodiments, the lens is an intraocular lens including at least two haptics engaged with an interior peripheral surface of the ciliary sulcus.

According to one or more embodiments, the step of implanting is performed by inserting the device through an incision created by phacoemulsification cataract surgery.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Figure 1:
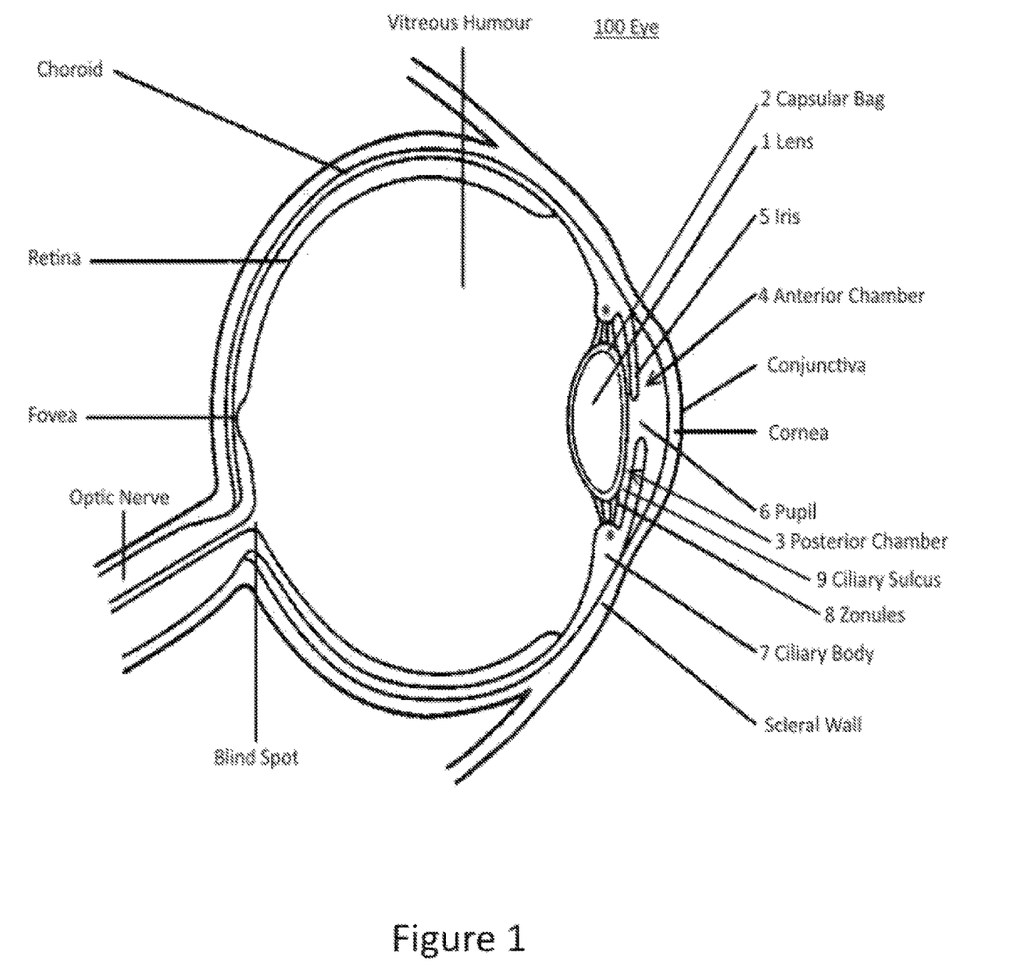
FIG. 1 is cross-section view of the human eye.

Referring generally to FIG. 1, the present relates to a device for implantation into an eye 100. In a normal human eye 100, as depicted in FIG. 1, the lens 1 is enveloped in the capsular bag 2 which is positioned centrally in the posterior chamber 3 of the eye 100 behind the iris 5 and aligned with the pupil 6. The capsular bag 2 is an elastic membrane or pouch having a generally circular cross-section, and is attached to the ciliary body 7 of the eye 100 through a series of zonules 8. The ciliary body 7 is attached to the scleral wall of the eye 100. The zonules 8 are thin fibers that function to centralize the capsular bag 2 and its enveloped lens 1 in a normal anatomic position within the posterior chamber 3 of the eye 100.

Figure 2:
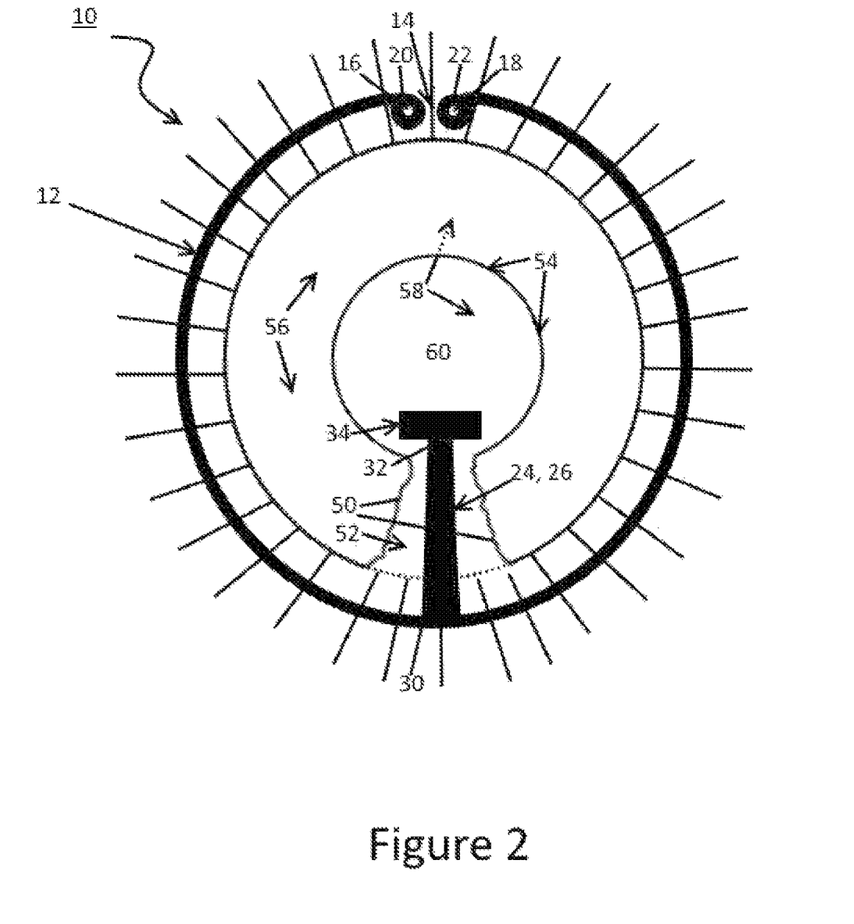
FIG. 2 is top view of the device including a spoke implanted in an eye according to one or more embodiments of the present invention.
Figure 4:
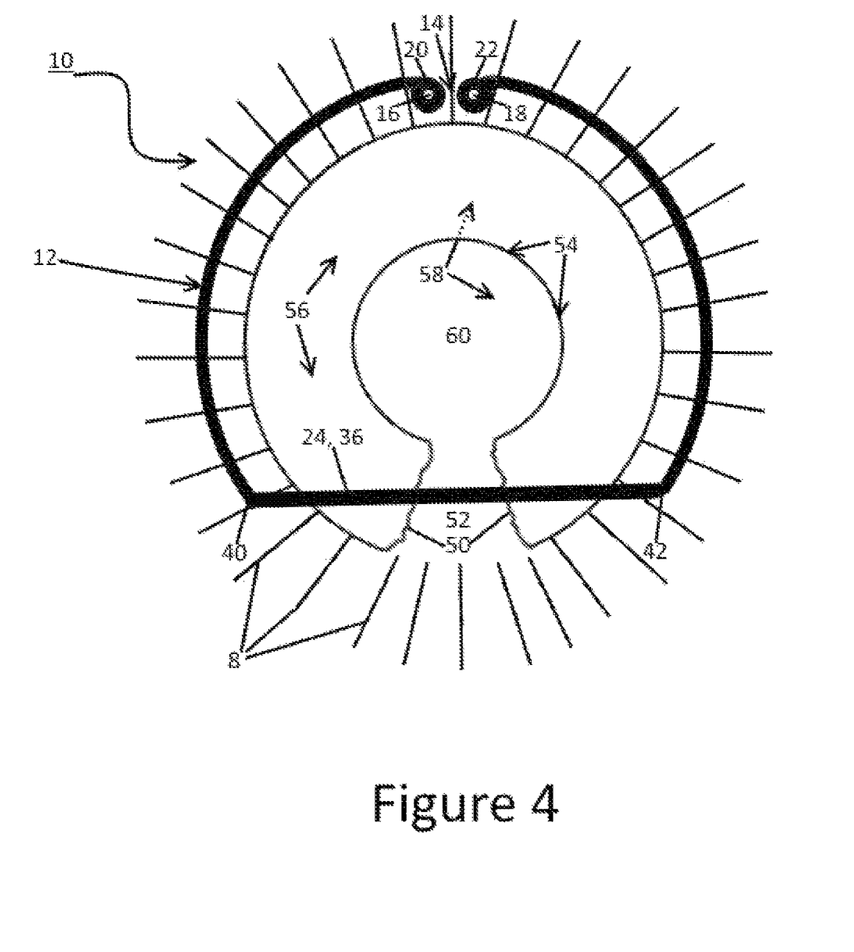
FIG. 4 is a top view of the device including a chord implanted in an eye according to one or more embodiments of the present invention.
Figure 5:
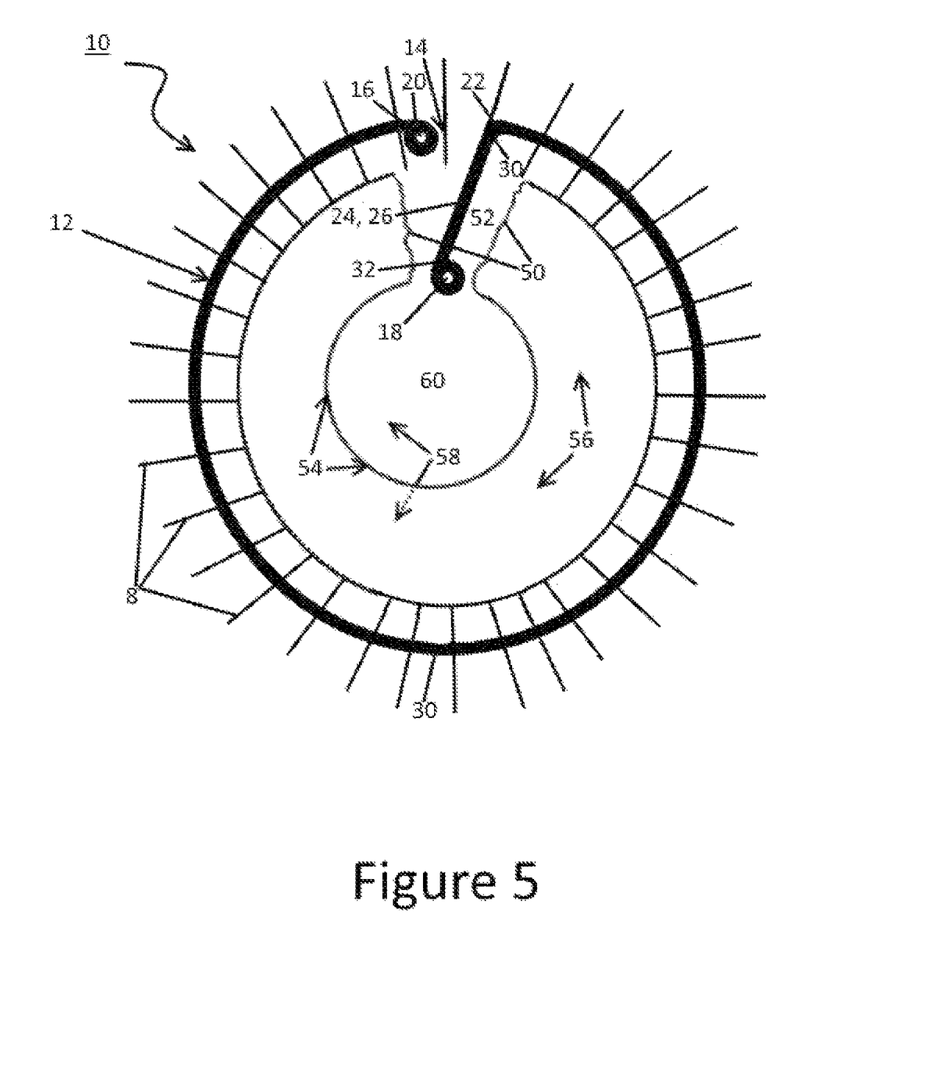
FIG. 5 is a top view of the device including a spoke implanted in an eye according to one or more embodiments of the present invention.

In patients suffering from a tear in the CCC (continuous curvilinear capsulorhexis) during cataract surgery, as illustrated by the tear 50 in FIGS. 2, 4 and 5, the CCC may become unstable and unable to support the intraocular lens (IOL) 44 in the ciliary sulcus 9 or posterior chamber 3 of the eye 100 since the tear(s) 50 extend to the posterior portion of the capsular bag 2 as well. The missing portion 52 of the capsular bag 2 may allow the IOL 44 to shift or drift into the vitreous humour of the eye 100 or be decentralized, thereby resulting in general decentration of the lens 44 and an unstable intraocular environment.

As is shown in FIGS. 2, 4 and 5, the device 10 of the present invention may be adapted to be implanted in the sulcus 9 for long-term stabilization of the IOL 44 during and after intraocular surgery. The capsular bag 2 of FIG. 1 is fully intact and envelopes the lens 1 of the eye 100, but following intraocular surgery to remove a cataractous lens, only a residual capsular bag 2 remains. As discussed SUPRA, a capsular tear 50, as depicted in FIGS. 2 and 4, is a common occurrence during cataract surgery, causing the bag 2 to become unstable and unfit for implantation of a lens 44.

During the capsulorhexis surgical procedure, an incision is made in the anterior portion 56 of the capsular bag 2 to remove a generally circular mid-portion 60 of the anterior portion 56 of the capsular bag 26. Following this procedure, the residual capsular bag 2 includes a posterior portion 58, an annular capsular flap on the anterior portion 56, and a generally circular capsulorhexis edge 54. During an uncomplicated cataract surgery, the residual capsular bag 12 is able to support an artificial intraocular lens (IOL) 44. In situations where the CCC (continuous curvilinear capsulorhexis) tears, however, such as is depicted in FIGS. 2 and 4, the surgeon is unable to place the IOL 44 in the sulcus 9 or in the bag 2. The present invention is particularly suited to aid the surgeon in such situations.

FIGS. 2 and 4 depicts a device 10 for implantation into an eye 100 according to at least one embodiment of this invention. The device may include a ring 12 and at least one support 24 defined internally of the ring 12. The ring 12 may include an open portion 14 defined between a first eyelet 16 on a first end 20 and a second eyelet 18 on a second end 22. Alternatively, as depicted in FIG. 5, the ring 12 may include an open portion 14 defined between a first eyelet 16 on a first end 20 and a second end 22. The eyelets 16, 18 may be used to position the device 10 within the eye 100 using, for example, a bent-tip instrument.

Further, the ring 12 may be radially compressible, such that the open portion 14 between the two eyelets 16, 18, or between the first eyelet 16 and the second end 22, may be expanded and contracted when pressure is applied to the circumference of the ring 12.

By defining a ring 12 including an open portion 14, the device 10 is specifically adapted to be implanted into the sulcus 9 of the eye 100. More particularly, the device 10 may be positioned between the iris 5 and the torn flap of the anterior portion 56 of the capsular bag 2 to engage an inner peripheral surface of the sulcus 9 and to abut against a predetermined diameter of the sulcus 9 (see FIGS. 2, 4 and 5). Further, the support 24 may have a position on which a lens 44 may be nestably engaged with the at least one support 24 above a tear 50 in the capsular bag 2 of the eye 100, thereby providing support to the IOL 44 both during and following intraocular surgery.

As mentioned SUPRA, the ring 12 is generally flexible to resist compression in a radial direction within the sulcus 9. In one embodiment, the ring 12 has an unflexed diameter of about 12 mm and a radially inward flexed diameter of about 10 mm. As one skilled in the art would appreciate, the unflexed and flexed diameter may vary greatly without departing from the spirit or scope of the present invention. The ring's compressibility permits, inter alia, placement in the sulcus 9 such that the ring 12 engages the inner periphery of the sulcus 9.

FIG. 2 illustrates one or more embodiments of the invention wherein the at least one support 24 is a first spoke 26 defining a first edge 30 engaged with the ring 12 and extending centrally within the ring 12 to a second edge 32.

In some embodiments, the device 10 may further include a second spoke 26 positioned approximately 180 degrees from the first spoke 26 along the circumference of the ring 12, with both spokes 26 extending centrally. Alternatively, the device 10 may include a plurality of spokes 26 positioned along the circumference of the ring 12, with each of the spokes 26 extending centrally. The use of a two spokes 26 or a plurality of spokes 26 may be particularly useful in cases of severe tears 50 of capsular bag 2 where larger portions (e.g., greater than 90 degrees) of the CCC are compromised. The additional spokes 26 offer greater stabilization and centralization to the IOL 44 positioned in the sulcus 9.

Figure 3:
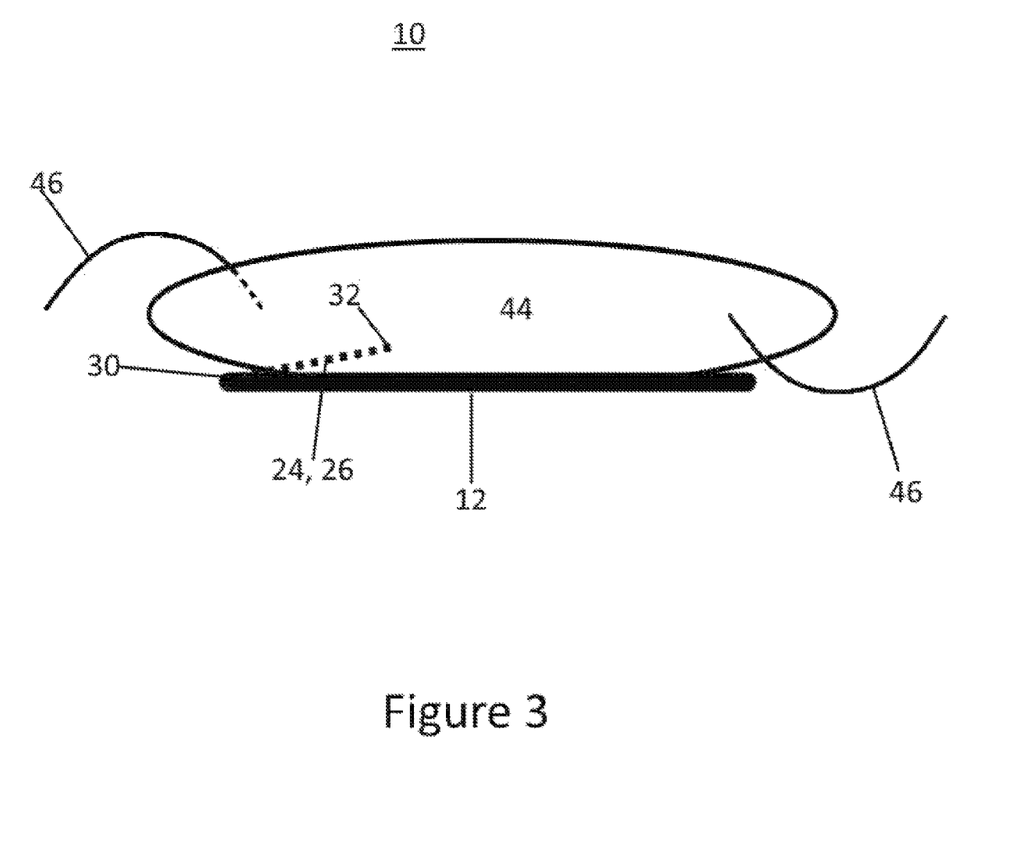
FIG. 3 is a side view of the device including a spoke according to one or more embodiments of the present invention.

According to one or more embodiments, any of the spokes 26 may be positioned substantially parallel to a plane formed by the circumference of the ring 12. In some embodiments, as depicted in FIG. 3, the first spoke 26 may be positioned at an angle relative to the plane formed by the circumference of the ring 12. The angle may be between 10 and 20 degrees, less than 10 degrees, or greater than 20 degrees. By angling the spoke 26 anteriorly, greater support may be offered to the IOL 44 by counteracting the pressure of the IOL 44 after positioning, thereby minimizing the risk of the IOL 44 dislocating in the future.

In one or more embodiments, the second edge 32 of the first spoke 26 is engaged with a central point of a segment 34 positioned perpendicular to the first spoke 26, thereby forming a "T" shape using the spoke 26 and the segment 34. The additional segment 34 advantageously offers greater support and stability to the lens 44 during and after surgery. In some embodiments, the segment 34 may be positioned in a plane parallel to the plane formed by the circumference of the ring 12. Any of the spokes 26 and segments 34 described herein may have a length, a width, and a shape. In some embodiments the length is between 3 mm and 6 mm, while in other embodiments the length is approximately 4.5 mm. In some embodiments the width is approximately 0.5 mm. The shape may be rectangular, triangular, tubular, or arced. As one skilled in the art would appreciate, the length, the width and the shape may vary widely without departing from the spirit or scope of the present invention. Further, the width, length and shape may be vary in relation to the number and position of spokes 26 and segments 34.

FIG. 4 depicts the device 10 including a ring 12 and at least one support 24, wherein the at least one support 24 is a chord 36 engaged with, and extending between, a third end 40 and a fourth end 42 of the ring 12. In other words, the ring 12 may extend circumferentially from the first end 20 to the second end 22, except that the chord 36 disrupts the circumferential nature of the ring 12 at a third end 40 and fourth end 42; instead the chord 36 extends within the circumference of the ring 12. The chord 36 may be substantially straight, arced, curved, or undulating. Further the engagement of the chord 36 and the ring 12 at the third end 40 and fourth end 42 may be curved, thereby minimizing risk of further damage to the eye 100 during insertion and while positioned therein.

As with the spoke embodiments, the device 10 including a chord 36 may be positioned such that the chord 36 extends across the tear 50 and/or the missing portion 52 of the capsular bag 2, thereby offering greater stabilization and centralization to the IOL 44 positioned in the sulcus 9. Also, as with the spoke embodiments, the chord embodiments of the device 10 may vary in length, width and shape. In one embodiment the width of the chord 36 is 0.5 mm. In some embodiments the chord 36 may be positioned substantially parallel to a plane formed by the circumference of the ring 12. In alternative embodiments, at least a portion of the chord 36 may be positioned outside of the plane formed by the circumference of the ring 12. For example, an arced or undulating chord 36 may have portions positioned outside of the ring's circumferential plane or may be positioned wholly within the ring's circumferential plane.

FIG. 5 illustrates a device 10 for implantation into an eye 100 including a ring having an open portion 14 defined between a first eyelet 16 on a first end 20 and a second end 22. In such an embodiment, the at least one support 24 may define a first edge 30 engaged with the second end 22 of the ring 12 and extending centrally within the ring 12 to a second edge 32 including a second eyelet 18. The device 10 depicted in FIG. 5, according to alternative embodiments, may also include any number of spokes 26 or chords 36, as described SUPRA.

In one or more embodiments, the device 10, and/or some or all of its components, may be made of biocompatible material. In some embodiments, the biocompatible material is polymetheylmethacrylate (PMMA), although those skilled in the art will appreciate that other biocompatible materials suitable for implantation in a sulcus 9 are also available.

Figure 6:
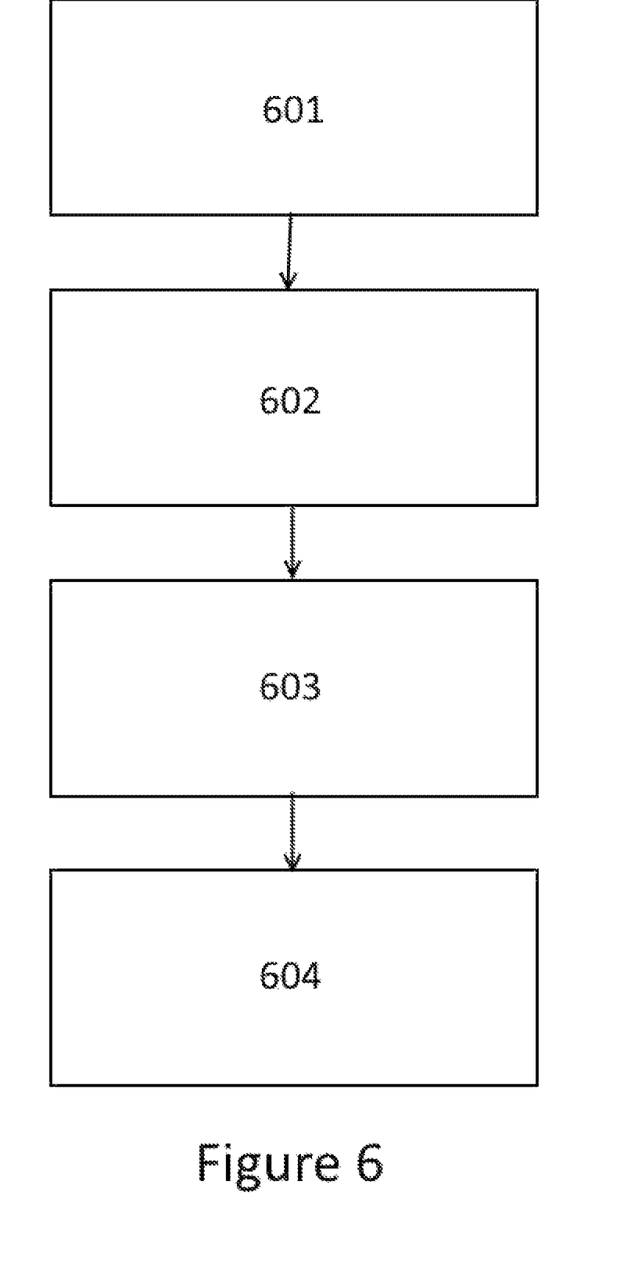
FIG. 6 is a flow chart illustrating the method of implanting the device into an eye according to one or more embodiments of the present invention.

FIG. 6 illustrates a method of implanting a device 10 into an eye 100. The method includes, in step 601, providing a device 10 according to any of the embodiments described herein. Further, the method may include, in step 602, implanting the device 10 into the ciliary sulcus 9 between the iris 5 and the capsular bag 2 of the eye 100. Implanting may be performed by inserting the device 10 through an incision created by phacoemulsification cataract surgery, as described SUPRA. The incision may be 1 mm in length, but may also be slightly smaller or much larger.

The method may further include, in step 603, positioning the at least one support 24 proximal to the tear 50, thereby providing stabilization and centralization to a lens 44 implanted into the eye 100 thereafter. The device 10 may be positioned anterior to a tear 50 in the capsular bag 2 of the eye 100. Further, the device 10 may be positioned in a circumferential manner within the sulcus 9 such that at least one support 24 is positioned proximal to the tear 50 and/or missing portion 52 of the capsular bag 2. The ring 12 of the device 10 may be engaged with an interior peripheral surface of the ciliary sulcus 9.

Following implantation of the device 10 into the ciliary sulcus 9, the method may further include, in step 604, placing a lens 44 in the ciliary sulcus 9 anterior to, and engaged with, the at least one support 24. The lens 44 may be an intraocular lens (IOL) including at least two haptics 46 engaged with an interior peripheral surface of the ciliary sulcus 9. The placement of the IOL 44 may include placing the haptics 46 in a position proximal to the portions of the capsular bag 2 which are not torn 50 or missing 52.

The invention claimed is:

1. A device for implantation into an eye, comprising:
 a ring having an open portion defined between a first end and a second end, the ring being radially compressible;
 at least one support defined internally of the perimeter of the ring and having a position for nestably engaging a lens, the at least one support being positioned above a tear in a capsular bag of the eye;
 the at least one support is a chord engaged with, and extending between, a third end and a fourth end of the ring, where the third and the fourth ends lie on a circumference of the ring, and the circumference of the ring lies within a plane;
at least, one portion of the ring is circular and the at least one support chord is a straight chord.

2. The device of claim 1, wherein the device is made of biocompatible material.

3. The device of claim 2, wherein the biocompatible material is polymethylmethacrylate.

4. The device of claim 1, wherein:
 the ring further includes a first eyelet on the first end and a second eyelet on the second end.

5. The device of claim 1, wherein:
 the chord is adapted for providing resting support of an interior of a posterior facing side of the lens.

6. The device of claim 1, wherein
 the perimeter of the ring has the circumference and the circumference is smaller than a circumference of the lens, which is supported on the ring.

7. The device of claim 1, wherein
 a shape of the ring is not a complete round circle.

8. The device of claim 1, wherein:
 the engagement of the chord and the ring at the third end and the fourth end is curved, thereby minimizing risk of further damage to the eye.

* * * * *